(12) United States Patent
Dinkelborg et al.

(10) Patent No.: US 6,436,365 B2
(45) Date of Patent: *Aug. 20, 2002

(54) PROCESS FOR THERAPEUTIC TREATMENT OF PROLIFERATIVE DISEASES

(75) Inventors: Ludger Dinkelborg; Stephan Christoph Hilger; Dieter Heldmann; Friedhelm Blume, all of Berlin (DE)

(73) Assignee: Schering Aktiengesellschaft, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/157,979

(22) Filed: Sep. 22, 1998

Related U.S. Application Data (60) Provisional application No. 60/062,261, filed on Oct. 17, 1997.

(51) Int. Cl.[7] .................... A61K 51/00; A61M 36/14
(52) U.S. Cl. .................. 424/1.65; 424/1.11; 424/9.1; 534/14
(58) Field of Search .............. 424/1.11, 1.65, 424/9.1, 9.3, 9.4, 9.5, 9.6, 9.7, 9.8, 450, 1.69; 534/7, 10–16; 530/300; 604/54, 52; 600/1–8

(56) References Cited

U.S. PATENT DOCUMENTS

| | | | | |
|---|---|---|---|---|
| 5,095,111 A | * | 3/1992 | Lever et al. ................. 540/544 |
| 5,279,811 A | * | 1/1994 | Bergstein et al. .......... 424/1.11 |
| 5,356,633 A | * | 10/1994 | Woodle et al. .............. 424/450 |
| 5,431,900 A | * | 7/1995 | Bergstein et al. .......... 424/1.65 |
| 5,634,895 A | * | 6/1997 | Igo et al. ...................... 604/52 |
| 5,681,278 A | * | 10/1997 | Igo et al. ...................... 604/52 |
| 5,688,485 A | * | 11/1997 | Harris ....................... 424/1.65 |
| 5,770,179 A | * | 6/1998 | Dean ......................... 424/1.73 |
| 5,858,990 A | * | 1/1999 | Walsh ......................... 514/44 |
| 5,891,084 A | * | 4/1999 | Lee ............................. 604/54 |
| 5,924,973 A | * | 7/1999 | Weinberger .................... 600/3 |

OTHER PUBLICATIONS

Liu et al., Appl. Radiat. Isot., vol. 48, No. 8, pp. 1103–1111, "99MTC–labeling Kinetics of Four Thiol–containing Chelators and 2–Hydra–Zinopyridine: Factors Influencing Their Radiolabeling Efficiency". Aug. 1997.*

"Local Delivery of Biodegradable MicroParticles Containing Colchicine or a Colchicine Analogue: Effects on Restenosis and Implications for Catheter–Based Drug Delivery" Gradus–Pizlo, et al., JACC, vol. 26, No. 6, Nov. 15, 1995; pp. 1549–1557.

"Handbook of Vascular Brachytherapy," J. Weinberger, edited by Waksman and Serruys.

* cited by examiner

Primary Examiner—Dameron L. Jones
(74) Attorney, Agent, or Firm—Millen, White, Zelano & Branigan, P.C.

(57) ABSTRACT

The invention relates to a process for therapeutic treatment of proliferative diseases, which is characterized in that first an administration catheter is placed on the site of the lesion, and a radioactive substance is administered topically via the catheter, then the catheter is again removed, and the radioactive substance remains on the site of the lesion.

17 Claims, 3 Drawing Sheets

PROCESS FOR THERAPEUTIC TREATMENT OF PROLIFERATIVE DISEASES

This application claims the benefit of U.S. Provisional Application No. 60/062,261, filed Oct. 17, 1997.

The invention pertains to the field of treatment of proliferative diseases and especially the treatment of vascular diseases such as, for example, arteriosclerosis.

It is known that ionizing radiation inhibits the proliferation of cells. A considerable number of neoplastic and non-neoplastic diseases have already been treated in this way (Fletcher, Textbook of Radiotherapy, Philadelphia, Pa.: Lea and Febiger, 1980, Hall, Radiobiology for the Radiologist, Philadelphia, Pa.: Lippincott, 1988).

An attempt has also already been made to treat arteriosclerotic diseases using this process. Arteriosclerosis is an inflammatory, fibroproliferative disease that is responsible for 50% of all deaths in the USA, Europe, and Japan (Ross 1993, Nature 362: 801–809). In its peripheral manifestation, it threatens the upkeep of the extremities; with its coronary manifestation, the risk of fatal myocardial infarction exists; and with supra-aortic infection, there is the threat of stroke.

At this time, arteriosclerosis is treated in various ways. In addition to conservative measures (e.g., lowering the cholesterol level in the blood) and the bypass operation, mechanical dilatation (angioplasty), as well as the intravascular removal of atheromatous tissue (atherectomy) of stenotic segments in peripheral arteries and the coronaries have been established as alternatives in regular clinical practice.

As stated below, the above-mentioned methods are associated with a considerable number of drawbacks, however.

The value of mechanical recanalization processes is greatly diminished by vascular occlusions as a result of vascular tears and dissections, as well as acute thromboses (Sigwart et al. 1987, N. Engl. J. Med. 316: 701–706). Long-term success is jeopardized by the reoccurrence of constrictions (restenosis). The CAVEAT study thus revealed that of 1012 patients, the restenosis rate six months after intervention in coronary atherectomy was 50% and in coronary angioplasty even 57% (Topol et al. 1993, N. Engl. J. Med. 329: 221–227). In addition, abrupt vascular occlusion occurred in this study in 7% of the atherectomy patients and in 3% of the angioplasty patients. Nicolini and Pepine (1992, Endovascular Surgery 72: 919–940) report a restenosis rate of between 35 and 40% and an acute occlusion rate of 4% after angioplastic intervention.

To combat these complications, various techniques have been developed. These include the implantation of metal endoprostheses (stents), (Sigwart et al. 1987, N. Engl. J. Med. 316: 701–706; Strecker et al., 1990, Radiology 175: 97–102). The implantation of stents in large-caliber arteries, e.g., in occlusions in the axis in the pelvis, has already become a treatment modality that is to be applied primarily. The use of stents in femoral arteries has shown disappointing results, however, with a primary openness rate of 49% and a reocclusion frequency of 43% (Sapoval et al., 1992, Radiology 184: 833–839). Similar unsatisfactory results have been achieved with currently available stents in coronary arteries (Kavas et al. 1992, J. Am. Coll. Cardiol. 20: 467–474).

Up until now, no pharmacological or mechanical interventions have been able to prevent restenosis (Muller et al. 1992, J. Am. Coll. Cardiol. 19: 418–432, Popma et al. 1991, Circulation 84: 14226–1436).

The reason for the restenoses frequently occurring after mechanical intervention is assumed to be that interventions induce a proliferation and migration of unstriped muscle cells in the vascular wall. The latter result in a neointimal hyperplasia and the observed restenoses in the treated vessel sections (Cascells 1992, Circulation 86, 723–729, Hanke et al. 1990, Circ. Res. 67, 651–659, Ross 1986, Nature 362, 801–809, Ross 1993, Nature 362, 801–809).

An alternative process for treating arteriosclerotic diseases uses ionizing radiation. The use of ionizing radiation of external origin on restenosis is associated with the drawback, however, that upon administration the radiation dose is not limited just to the desired spot; rather, the surrounding (healthy) tissue is also undesirably exposed to the radiation. Thus, to date, various studies have come up with little to increase the chances of success (Gellmann et al. 1991, Circulation 84 Suppl. II: 46A-59A, Schwartz et al. 1992, J. Am. Coll. Cardiol. 19: 1106–1113).

These drawbacks, which occur when external radiation sources are used, can be overcome if gamma radiation is directly used with restenosis via, e.g., a catheter in the vascular area. With this form of administration with iridium-192, a high radiation dose of 20 Gy is applied to the restenosis foci. Some works report on the almost complete prevention of restenosis after this intervention (Wiedermann et al. 1994, Am. J. Physiol. 267: H125-H132, Böttcher et al. 1994, Int. J. Radiation Oncology Biol. Phys. 29: 183–186, Wiedermann et al. 1994 , J. Am. Coll. Cardiol. 23: 1491–1498, Liermann et al. 1994, Cardiovasc. Intervent. Radiol. 17: 12–16). A drawback to this method is, however, that the radiation dose of 20 Gy that is applied in this case is very high. Since the lesions are dispersed irregularly on the vascular wall, uniform administration of a defined dose is not possible using this technique. Moreover, treatment of large-caliber vessels is not possible since, because of the dose reduction from the iridium source, the dose that can be administered is not adequate.

Another possible way of inhibiting restenosis is the implantation of P-32-doped stents (Fischell et al. Stents III, Entwicklung, Indikationen und Zukunft, Konstanz [Development, Indications, and the Future: Constancy]: Kollath and Liermann, 1995). In this work, an activity of 0.2 kBq P-32 per centimeter of stent length was enough (corresponding to a radiation dose of 0.25 Gy) to achieve maximum inhibition of unstriped vascular muscle cells in vitro. It was thus possible to show that not only γ-emitters but also β-emitters prevent the proliferation of unstriped muscle cells. An advantage of this method is that the radiation dose administered is considerably lower than in all previously mentioned interventions. At this low dose, the endothelial cells that line the vascular bed are not damaged (Fischell et al. Stents III, Entwicklung, Indikationen und Zukunft, Konstanz: Kollath and Liermann, 1995). This form of intervention can be used only once, however, namely when the stent is positioned. In addition, it is limited only to those interventions in which stents are used. The restenoses that occur in the far more common types of interventions, such as atherectomies and angioplasties, cannot be treated with this method. Because of the small range of action of the β-radiation, it is not possible to administer a uniform dose of energy to the entire lesion.

In addition to radiation therapy, a number of other therapeutic strategies are used for inhibiting neointimal hyperplasias (restenoses). The latter comprise standard medicines for suppression of restenoses such as antithrombotic agents, platelet aggregation inhibitors, calcium antagonists, anti-inflammatory and antiproliferative substances, but also gene-therapy approaches. In this case, the inhibition of growth stimulators, e.g., by antisense oligonucleotides or the enhancement of inhibiting factors by expression-vector-plasmids and the virus-mediated gene integration, is possible. Also, Aptamer oligonucleotides can be used for inhibiting a wide variety of receptor-mediated processes, which play a decisive role in restenosis.

With great energy and care, substances have been studied over the years that were administered under strictly controlled conditions as a long-term treatment since the desired purpose was theoretically to reduce the restenosis rate (Herrmann et al., 1993, Drugs 46: 18–52).

More than 50 controlled studies with different substance groups were performed, without yielding definite proof that the substances examined could seriously reduce the restenosis rate.

This also applies for topical administration, in which the substances are brought via a special balloon catheter to the site of action that is desired in each case. It has been shown, however, that the previously used substances are washed too quickly from the vascular wall to be able to be therapeutically effective. Moreover, additional vascular wall alterations, which even act to promote restenosis, are induced by these pressure-mediated liquid injections.

The object of this invention was therefore to develop a process for the treatment of proliferative diseases that overcomes the drawbacks of previously known treatment processes.

This object is achieved by this invention.

A process for therapeutic treatment of proliferative diseases was developed that is characterized in that first an administration catheter is placed at the site of the lesion, a radioactive substance is topically administered via the catheter, then the catheter is removed, and the radioactive substance remains at the site of the lesion.

Since radioactive substances are transported via an administration catheter right to the wall of a blood vessel and remain there, the concentration of the radionuclide lasts long enough to inhibit the proliferation of the cells and thus a restenosis.

The process according to the invention has some important advantages over known treatment processes. In comparison to a considerable number of studied compounds from a wide variety of classes, the topical administration of certain substances and with certain catheters results in a surprisingly high radioactive dose at the desired, pathologically altered spot. This procedure results in a highly effective radiation dose with a low systemic load. The radioactive substances have a long dwell time at the administration site, which results in a highly effective dose on the spot. They are dispersed in particular and uniformly in the pathological regions. The unbonded radioactive substances are quickly eliminated.

Since certain radioactive substances, which are described in more detail below, pass into the wall of the arteriosclerotically altered vessels, not only the cells of the intima that face the lumen, but also those of the media and adventitia are kept from proliferating. The portion of the administered dose that passes through the cell membrane results in a high radiation dose, which is effective close to the cell core.

Owing to the sensitivity of proliferating cells to ionizing radiation, the process according to the invention is suitable not only for treatment of arteriosclerotic diseases, but also for the treatment of other proliferative diseases, such as, e.g., tumor diseases.

Suitable radioactive substances are those that have sufficiently high lipophilia to remain adhered to the plaque. For example, radiolabeled metal complexes are suitable, such as, e.g., metal complexes of bis-amine-oxime derivatives of general formula I

(I)

in which n=0–3, and radicals $R^1$ to $R^8$ are the same or different and in each case stand for a hydrogen atom and/or for an unbranched, branched, cyclic or polycyclic $C_1$–$C_{100}$ alkyl, $C_1$–$C_{100}$ alkenyl, $C_1$–$C_{100}$ alkinyl, $C_1$–$C_{100}$ aryl, $C_1$–$C_{100}$ alkylaryl and/or $C_1$–$C_{100}$ arylalkyl radical, which optionally is substituted with fluorine, chlorine, bromine and/or iodine atoms, and/or hydroxy, oxo, carboxy, aminocarbonyl, alkoxycarbonyl, amino, aldehyde or alkoxy groups with up to 30 carbon atoms and/or optionally is interrupted and/or substituted by one or more heteroatoms from the series N, P, As, O, S, Se, and whereby radicals $R^2$ and $R^3$, $R^4$ and $R^5$ as well as $R^6$ and $R^7$ together optionally can stand for an oxygen atom. These compounds, together with a radionuclide, form a metal complex, which is then used for topical administration in the treatment of proliferative diseases.

Also suitable are the metal complexes of the $N_2S_2$ derivatives of general formulas II and III (II)

(III)

whereby $R^9$ to $R^{32}$ are the same or different and in each case stand for a hydrogen atom or for an unbranched, branched, cyclic or polycyclic $C_1$–$C_{100}$ alkyl, $C_1$–$C_{100}$ alkenyl, $C_1$–$C_{100}$ alkinyl, $C_1$–$C_{100}$ aryl, $C_1$–$C_{100}$ alkylaryl and/or $C_1$–$C_{100}$ arylalkyl radical, which is optionally substituted with fluorine, chlorine, bromine, and/or iodine atoms and/or hydroxy, oxo, carboxy, aminocarbonyl, alkoxycarbonyl, amino, aldehyde, or alkoxy groups with up to 30 carbon atoms, and/or optionally is interrupted and/or substituted by one or more heteroatoms from the series N, P, As, O, S, Se, and whereby radicals $R^{11}$ and $R^{12}$, $R^{13}$ and $R^{14}$, $R^{15}$ and $R^{16}$, as well as $R^{17}$ and $R^{18}$ together optionally can stand for an oxygen atom, and n, m and p, independently of one another, mean 1 or 2.

Other suitable compounds, which are suitable for topical treatment after complexing with suitable radioisotopes, are tetrofosmin, sestamibi and furifosmin derivatives. $^{99m}$Tc-tetrofosmin can be obtained under the trade name Myoview™ from the Amersham Company; $^{99m}$Tc-sestamibi is marketed under the trade name Cardiolite® by the DuPont Company; and $^{99m}$Tc-furifosmin can be purchased under the trade name TechneScan Q-12 from the Mallinckrodt Medical Company.

Together with a radionuclide, all these compounds form a metal complex that can then be used for topical administration in the treatment of proliferative diseases.

To form a metal complex, radionuclides can be introduced that are alpha-, beta- and/or gamma-radiators, positron-radiators, Auger electron-radiators, and fluorescence radiators, whereby β- as well as combined β/γ-radiators are preferred for therapeutic purposes.

Corresponding radionuclides are known to one skilled in the art. By way of example, the radionuclides of the elements of atomic numbers 27, 29–32, 37–39, 42–51, 62, 64, 70, 75, 77, 82, or 83 can be mentioned.

Preferred are the nuclides $^{99m}$Tc, $^{186}$Re, $^{188}$Re, $^{67}$Cu, $^{90}$Y and $^{107}$Ag; especially preferred are nuclides $^{186}$Re, $^{188}$Re and $^{67}$Cu.

The production of bis-amine-oxime derivatives is described in U.S. Pat. Nos. 5,506,345 and 5,387,692; the production of $N_2S_2$ derivatives is described in U.S. Pat. No. 5,279,811.

The production of tetrofosmin derivatives is described in European Patent Application EP 303 374; the production of furifosmin derivatives is described in U.S. Pat. No. 5,112,595. Sestamibi derivatives and their production are described in International Patent Application WO 89/02433.

Other suitable metal complexes have ligands that are derived from ethylenediaminetetraacetic acid (EDTA), diethylenetriaminepentaacetic acid (DTPA), or a macrocyclic compound, such as, e.g., tetraazacyclododecane. The production of these compounds is known to one skilled in the art and is, moreover, described in detail in the examples below.

Other suitable ligands are, e.g., porphyrin derivatives, as they are described in, e.g., DE 42 32 925 A1 and DE 43 05 523 A1. Metal complexes that are suitable for the process according to the invention can also be produced with radionuclides from these ligands.

Also suitable are radioactive thallium compounds of isotopes $^{201}$Tl, $^{207}$Tl, $^{209}$Tl, and $^{210}$Tl; especially suitable is $^{201}$TlCl.

Radiolabeled colloidal solutions are also extremely well suited for the treatment of proliferative diseases and especially for topical administration.

Suitable colloidal solutions are the tin colloids that are described in the examples; especially suitable are the tin colloids that can be produced with the aid of a kit from the Amersham Company ("Amerscan Zinnkolloid ($^{99m}$Tc)—Markierungskit für die Leberszintigraphie [Amerscan Tin Colloid ($^{99m}$Tc)—Labeling Kit for Liver Scintigraphy])." Other suitable colloids are, e.g., radioactive gold sol ($^{198}$Au colloid) and radiolabeled sulfur colloids as well as other physiologically compatible, radioactive colloidal solutions.

Suitable radionuclides for radioactive labeling of colloidal solutions are known to one skilled in the art. By way of example, the radionuclides of elements Ag, As, At, Au, Ba, Bi, Br, C, Co, Cr, Cu, F, Fe, Ga, Gd, Hg, Ho, I, In, Ir, Lu, Mn, N, O, P, Pb, Pd, Pm, Re, Rh, Ru, Sb, Sc, Se, Sm, Sn, Tb, Tc, or Y can be mentioned.

Preferred are the nuclides $^{99m}$Tc, $^{186}$Re, $^{188}$Re, $^{67}$Cu, $^{90}$Y, $^{153}$Sm, $^{160}$Tb, $^{162}$Tb, $^{198}$Au, and $^{107}$Ag.

The production of the colloidal solutions is generally done with a redox reaction or the alteration of pH in an aqueous or alcoholic solution in the presence of a radioactive salt. The colloid can be formed in the presence of a stabilizer or subsequently mixed with a surfactant or another stabilizing amphiphilic substance. Other production methods for suitable colloidal solutions are electrochemical methods, such as are described by, e.g., M. T. Reetz et al. in Angew. Chem. [Applied Chemistry] 1995, Vol. 107, p. 2461 ff. The production of the tin colloids is described in the examples below, as well as in the instructions of the labeling kit of the Amersham Company. The production of a gold colloid for diagnostic purposes is described in Patent DE 24 20 531 C3.

The size of the particles formed is in the range between 5 and 1000 nm, and in the case of the tin colloid it is between 300 and 600 nm.

Figure 3:
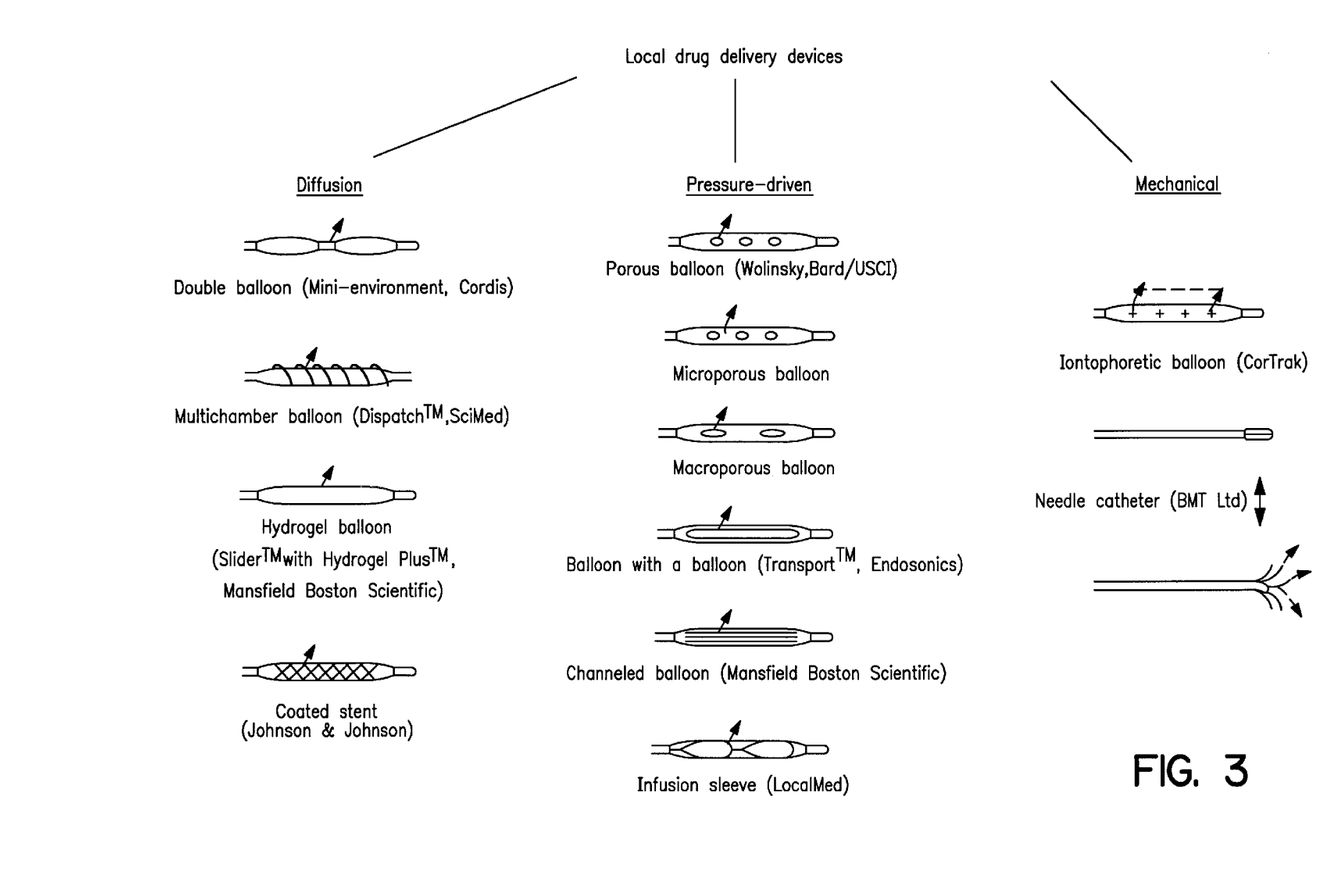
FIG. 3 shows local drug delivery devices.

As catheters that are suitable for topical administration of the substances according to the invention, the catheters that are sketched in FIG. 3 can be used. Especially suitable are multichamber balloon catheters (such as, e.g., Dispatch™, SciMed) and microperforated balloon catheters.

In the examples below, the process in the animal experiment is described. In addition, the production of some compounds that are suitable for use in this treatment process is described. In Examples 1 to 5, the process is implemented with $^{99m}$Tc-labeled HMPAO, whereby the ligand HMPAO has the following structure:

(see also Radiopharmaceuticals, Chemistry and Pharmacology, edited by Adrian D. Nunn, 1992, page 53).

EXAMPLE 1

Topical Administration of $^{99m}$Tc-HMPAO

The test animal, a white New Zealand rabbit (internal animal identification no.: 1708, male, 3.7 kg of body weight), was prepared 4 weeks before the actual administration experiment:

Under anesthesia (Rompun/Ketavet 1:2, 1 ml/kg of body weight, i.m. administration), the endothelium was damaged with a 2F Fogarthy balloon catheter in the arteria carotis dextra (balloon denudation). Then, the animal received a special diet with an addition of 0.2% cholesterol. The test animal developed an arteriosclerotic lesion on the balloon-denuded spot created by this pretreatment.

Topical administration of HMPAO that was labeled with technetium 99m was carried out on the anesthetized test animal (anesthesia type s.o.) via a coronary perfusion/infusion catheter (dispatch 3.0, Xtra slippery coating, manufacturer: Boston Scientific Corporation, Ratingen) directly on the lesion in the carotid artery. The radioactive dose of 0.48 mCi (=17.76 MBq) was administered in a volume of 0.85 ml.

During the entire experiment, the test animal was under a gamma camera (Elscint SP4 HR) to measure the dispersion of radioactivity in the body. The activity at the lesion was set as a proportion of the total activity (measured at this time in the animal). In the case of this test animal, there was found:

5 minutes post administration 55.38% of the dose at the lesion 4 hours post administration 46.78% of the dose at the lesion 24 hours post administration 21.45% of the dose at the lesion

EXAMPLE 2

Topical Administration of $^{99m}$Tc-HMPAO

The test animal, a white New Zealand rabbit (internal animal identification no.: 1856, male, 3.3 kg of body weight), was prepared 4 weeks before the actual administration experiment as follows:

Under anesthesia (Rompun/Ketavet 1:2, 1 ml/kg of body weight, i.m. administration), the endothelium was damaged with a 2F Fogarthy balloon catheter in the arteria carotis dextra (balloon denudation). Then, the animal received a special diet with an addition of 0.2% cholesterol. The test animal developed an arteriosclerotic lesion on the balloon-denuded spot created by this pretreatment.

The topical administration of the HMPAO that was labeled with technetium 99m was carried out on the anesthetized test animal (anesthesia type s.o.) via a coronary perfusion/infusion catheter (dispatch 3.0, Xtra slippery coating, manufacturer: Boston Scientific Corporation, Ratingen) directly on the lesion in the carotid artery. The radioactive dose of 1.91 mCi (=70.67 MBq) was administered in a volume of 1.0 ml (flushing with 0.3 ml of physiological saline solution).

During the entire experiment, the test animal was under a gamma camera (Elscint SP4 HR) to measure the dispersion of radioactivity in the body. The activity in the lesion was set as a proportion of the total activity (measured at this time in the animal). In the case of this test animal, there was found:

5 minutes post administration 40.74% of the dose at the lesion 4 hours post administration 35.13% of the dose at the lesion 24 hours post administration 23.69% of the dose at the lesion

EXAMPLE 3

Topical Administration of $^{99m}$Tc-HMPAO

The test animal was a white New Zealand rabbit (internal animal identification no.: 1584, male, 3.4 kg of body weight).

Under anesthesia (Rompun/Ketavet 1:2, 1 ml/kg of body weight, i.m. administration), the endothelium was damaged with a balloon catheter in the infraranal aorta (balloon denudation). Then, over a period of 5 minutes, technetium 99m-labeled HMPAO was administered to the test animal via a microperforated balloon catheter (4 mm Match-35 PTA, Schneider Company, FRG). The radioactive dose of 0.64 mCi (=23.68 MBq) was administered in a volume of 1 ml.

During the entire experiment, the test animal was under a gamma camera (Elscint SP4 HR) to measure the dispersion of radioactivity in the body. The activity in the lesion was set as a proportion of the total activity (measured at this time in the animal). In the case of this test animal, there was found:

5 minutes post administration 38.45% of the dose at the lesion 4 hours post administration 35.64% of the dose at the lesion 24 hours post administration 16.63% of the dose at the lesion

EXAMPLE 4

Topical Administration of $^{99m}$Tc-HMPAO

The test animal was a white New Zealand rabbit (internal animal identification no.: 1587, male, 3.5 kg of body weight).

Under anesthesia (Rompun/Ketavet 1:2, 1 ml/kg of body weight, i.m. administration), the endothelium was damaged with a balloon catheter in the infraranal aorta (balloon denudation). Then, over a period of 5 minutes, technetium 99m-labeled HMPAO was administered to the test animal via a microperforated balloon catheter (4 mm Match-35 PTA, Schneider Company, FRG). The radioactive dose of 1.18 mCi (=43.66 MBq) was administered in a volume of 1 ml.

During the entire experiment, the test animal was under a gamma camera (Elscint SP4 HR) to measure the dispersion of radioactivity in the body. The activity in the lesion was set as a proportion of the total activity (measured at this time in the animal). In the case of this test animal, there was found:

5 minutes post administration 37.06% of the dose at the lesion 4 hours post administration 32.03% of the dose at the lesion 24 hours post administration 20.01% of the dose at the lesion

EXAMPLE 5

Topical Administration of $^{99m}$TC-HMPAO

The test animal was a white New Zealand rabbit (internal animal identification no.: 1586, male, 3.3 kg of body weight).

Under anesthesia (Rompun/Ketavet 1:2, 1 ml/kg of body weight, i.m. administration), the endothelium was damaged with a balloon catheter in the infraranal aorta (balloon denudation). Then, over a period of 5 minutes, technetium 99m-labeled HMPAO was administered to the test animal via a microperforated balloon catheter (4 mm Match-35 PTA, Schneider Company, FRG). The radioactive dose of 0.45 mCi (=16.65 MBq) was administered in a volume of 1 ml.

During the entire experiment, the test animal was under a gamma camera (Elscint SP4 HR) to measure the dispersion of radioactivity in the body. The activity in the lesion was set as a proportion of the total activity (measured at this time in the animal). In the case of this test animal, there was found:

5 minutes post administration 45.56% of the dose at the lesion 4 hours post administration 36.39% of the dose at the lesion 24 hours post administration 15.24% of the dose at the lesion

EXAMPLE 6

Production of 1-{3-[N-(2-Methoxyethyl)-octadecylsulfamoyl]-2-hydroxy-propyl}-4,7,10-tetraaza-cyclododecane, Yttrium-90 Complex 5 mg of 1-{3-[N-(2-methoxyethyl)-octadecylsulfamoyl]-2-hydroxypropyl}-4,7,10-tetraazacyclododecane (produced according to DE 4340809.5) is dissolved in 500 µl of dimethyl sulfoxide and 50 µl of 0.1M sodium acetate buffer (pH=4.0). After 37 MBq of yttrium-90-trichloride solution is added, the reaction mixture is heated for 10 minutes to 100° C. The Y-90 complex solution that is thus prepared can be used without additional purification.

EXAMPLE 7 a) Production of N,N'-Bisundecyl-diethylene-triamine-pentaacetic acid Diamide 3.57 g (10 mmol) of diethylene-triamine-pentaacetic acid bisanhydride is suspended together with 4.05 g (40 mmol) of triethylamine in 100 ml of absolute dimethylformamide. Then, a solution of 3.42 g (20 mmol) of undecylamine, dissolved in 50 ml of absolute dichloromethane, is added in drops to the reaction mixture at room temperature. The reaction batch is stirred for 6 hours at room temperature, filtered and concentrated by evaporation in a medium-high vacuum. The residue is dissolved three times in 100 ml of dimethylformamide and concentrated by evaporation in a medium-high vacuum in each case. 50 ml of absolute diethyl ether is poured over the foamy reaction product, and it is stirred overnight. It is filtered and dried in a medium-high vacuum.

Yield: 6.3 g (90%), white powder.
Elementary analysis:
Cld: C 61.77 H 9.94 N 10.01 O 18.86
Fnd: C 61.52 H 9.63 N 9.91 O b) Production of N,N'-bisundecyl-diethylenetriamine-pentaacetic acid diamide, yttrium-90 complex 5 mg of N,N'-bisundecyl-diethylenetriamine-pentaacetic acid diamide (Example 7a) is dissolved in 500 µl of dimethyl sulfoxide and 50 µl of 0.1M sodium acetate buffer (pH=4.0). After 37 MBq of yttrium-90 trichloride solution is added, the reaction mixture is allowed to stand for 10 minutes at room temperature. The Y-90 complex solution that is thus prepared can be used without additional purification.

EXAMPLE 8 a) Production of N-Benzyloxycarbonyl-glycyl-N'-undecyl-glycinamide 3.63 g (10 mmol) of N-benzyloxycarbonyl-glycyl-glycine-N-hydroxysuccinimide ester and 1.71 g (10 mmol) of undecylamine are dissolved in 100 ml of absolute dichloromethane. The reaction mixture is stirred for 6 hours at room temperature. Then, it is diluted with 100 ml of dichloromethane, the organic phase is washed twice with 50 ml of saturated sodium bicarbonate solution and once with 50 ml of water. It is dried on magnesium sulfate, and the solvent is evaporated in a vacuum. The crude product is purified by chromatography on silica gel (eluent: dichloromethane/methanol 95:5).

Yield: 3.8 g (90.6%), white powder.
Elementary analysis:
Cld: C 65.84 H 8.89 N 10.01 O 15.25
Fnd: C 65.71 H 9.02 N 10.10 O b) Production of Glycyl-N'-undecyl-glycinamide 3 g (7.15 mmol) of N-benzyloxycarbonyl-glycyl-N'-undecyl-glycinamide (Example 8a) is dissolved in 100 ml of absolute ethanol. After 300 mg of palladium is added to carbon (10%), it is hydrogenated for 2 hours at room temperature (1 atmosphere of hydrogen). It is filtered and concentrated by evaporation in a vacuum. The resulting amine is used for subsequent reaction without additional purification.

Yield: 1.92 g (94.1%), white foam.
Elementary analysis:
Cld: C 63.12 H 10.95 N 14.72 O 11.21
Fnd: C 63.03 H 11.04 N 14.57 O c) Production of N-(S-Acetyl-mercaptoacetyl)-glycyl-N'-undecyl-glycinamide 285.4 mg (1 mmol) of glycyl-N'-undecyl-glycinamide (Example 8b) and 231.2 mg (1 mmol) of S-acetyl-mercapto-acetic acid-N-hydroxy-succinimide ester are dissolved together in 20 ml of absolute dichloromethane. The reaction mixture is stirred for 6 hours at room temperature. Then, it is diluted with 20 ml of dichloromethane, and the organic phase is washed twice with 5 ml of semi-saturated sodium bicarbonate solution and once with 5 ml of water. It is dried on magnesium sulfate, and the solvent is evaporated in a vacuum. The crude product is purified by chromatography on silica gel (eluent: dichloromethane/methanol 93:7).

Yield: 362 mg (90.1%), white powder
Elementary analysis:
Cld: C 56.83 H 8.79 N 10.46 O 15.94 S 7.98
Fnd: C 56.67 H 8.93 N 10.18 O S 7.72 d) Production of N-(Mercaptoacetyl)-glycyl-N'-undecyl-glycinamide 201 mg (0.5 mmol) of N-(S-acetyl-mercaptoacetyl-glycyl-N'-undecyl-glycinamide (Example 8c) is dissolved in 15 ml of absolute ethanol. It is saturated with argon, and an ammonia stream is directed through the solution for 30 minutes. Then, it is concentrated by evaporation, and the residue is taken up in 20 ml of dichloromethane. The organic phase is shaken once with 2% aqueous citric acid and dried on sodium sulfate. The solvent is evaporated in a vacuum, and the residue is chromatographed on silica gel (eluent: dichloromethane/methanol 9:1).

Yield: 153 mg (85.1%), white powder
Elementary analysis:
Cld: C 56.79 H 9.25 N 11.69 O 13.35 S 8.92
Fnd: C 56.67 H 9.43 N 11.48 O S 8.71 e) Production of N-(Mercaptoacetyl)-glycyl-N'-undecyl-glycinamide, Re-186 Complex 5 mg of N-(mercaptoacetyl)-glycyl-N'-undecyl-glycinamide (Example 8d) is dissolved in 800 µl of ethanol. After 5 mg of disodium-L-tartrate and 50 µl of 0.1 M sodium hydrogen phosphate buffer (pH=8.5) are added, 37 MBq of perrhenate and 10 µl of tin dichloride-dihydrate solution (5 mg of $SnCl_2 \times 2H_2O$/1 ml of 0.1 M HCl) are added. The reaction mixture is heated for 5 minutes to 60° C. The thus prepared solution of the Re-186 complex of N-(mercaptoacetyl)-glycyl-N'-undecyl-glycinamide can be used without additional purification.

EXAMPLE 9

Production of N,N'-Bis[3,6,9,9-tetra (hydroxycarboxymethyl)-1-oxo-3,6,9-triaza-non-1-yl]-mesoporphyrin-IX-13,17-dihydrazide, Y-90 Complex 5 mg of N,N'-bis[3,6,9-tri(hydroxycarboxymethyl)-9-(ethoxycarboxymethyl)-1-oxo-3,6,9-triaza-non-1-yl]-mesoporphyrin-IX-13,17-dihydrazide (produced according to DE 42 32 925 A1, Example 1a) is stirred in 5 ml of 0.1M NaOH under argon atmosphere for 3 hours at room temperature. After saponification of the bis-ethyl ester (TLC monitoring) has been completed, it is set at pH=6 with glacial acetic acid, and 37 MBq of yttrium-90-trichloride solution is added to the batch. It is stirred for 15 minutes at room temperature. HPLC analysis indicates 95% incorporation of the radioisotope.

EXAMPLE 10

Production of 5,10,15,20-Tetrakis-[3-(carboxymethoxy)-phenyl]-porphyrin, Yttrium-90 Complex 2.0 mg of 5,10,15,20-tetrakis-[3-(carboxymethoxy)-phenyl]-porphyrin (produced according to DE 43 05 523 A1, Example 13a) is dissolved in 5 ml of acetic acid and mixed with a hydrochloric acid solution of 1.0 mCi yttrium-90-chloride. The reaction mixture is autoclaved for one hour at 140° C., the solvent is evaporated in a vacuum, and the residue is taken up in 5 ml of water. By adding aqueous sodium bicarbonate solution in drops, it is set at pH 7.3, and the red solution that is produced is filtered with a membrane filter. HPLC monitoring of the filtrate indicates an incorporation rate of >95% of the activity used in the porphyrin ligands.

EXAMPLE 11

Production of 5,10,15,20-Tetrakis-[3-(carboxymethoxy)-phenyl]-porphyrin, Copper-67 Complex The production of the complex is described in DE 43 05 523 A1, Example 14.

EXAMPLE 12

Production of a Technetium-99m-tin Colloid

555 MBq of sodium pertechnetate-99m in 2 ml of 0.9% sodium chloride solution is mixed at room temperature with 20 µl of tin(II) chloride solution (5 mg of tin(II) chloride-dihydrate/1 ml of 0.01 M HCl). After 10 minutes, it is diluted with 1 ml of PBS buffer. The solution that is obtained is slightly opalescent.

EXAMPLE 13

Production of a Rhenium-186-tin Colloid

37 MBq of sodium perrhenate-186 in 2 ml of 0.9% sodium chloride solution is mixed at room temperature with 40 µl of tin(II) chloride solution (5 mg of tin(II) chloride dihydrate/1 ml of 0.01 M HCl). After 10 minutes, it is diluted with 1 ml of PBS buffer. The solution that is obtained is slightly opalescent.

EXAMPLE 14

Topical Administration of a Tin Colloid

The test animal is a white New Zealand rabbit (internal animal identification no.: 1852, male, 3.5 kg of body weight).

Under anesthesia (Rompun/Ketavet 1:2, 1 ml/kg of body weight, i.m. administration), the endothelium was damaged with a balloon catheter in the infraranal aorta (balloon denudation). Then, over a period of 5 minutes, tin colloid, which was produced according to the kit of the Amersham Company ("Amerscan Zinnkolloid ($^{99m}$Tc)— Markierungskit für die Leberszintigraphie [Amerscan Tin Colloid ($^{99m}$Tc)—Labeling Kit for Liver Scintigraphy]"), was administered to the test animal with a microperforated Match catheter (balloon catheter with a 5 mm diameter; manufacturer: Schneider Company, Düsseldorf). The radioactive dose of 0.4 mCi (=14.8 MBq) was administered in a volume of 0.1 ml.

Figure 1:
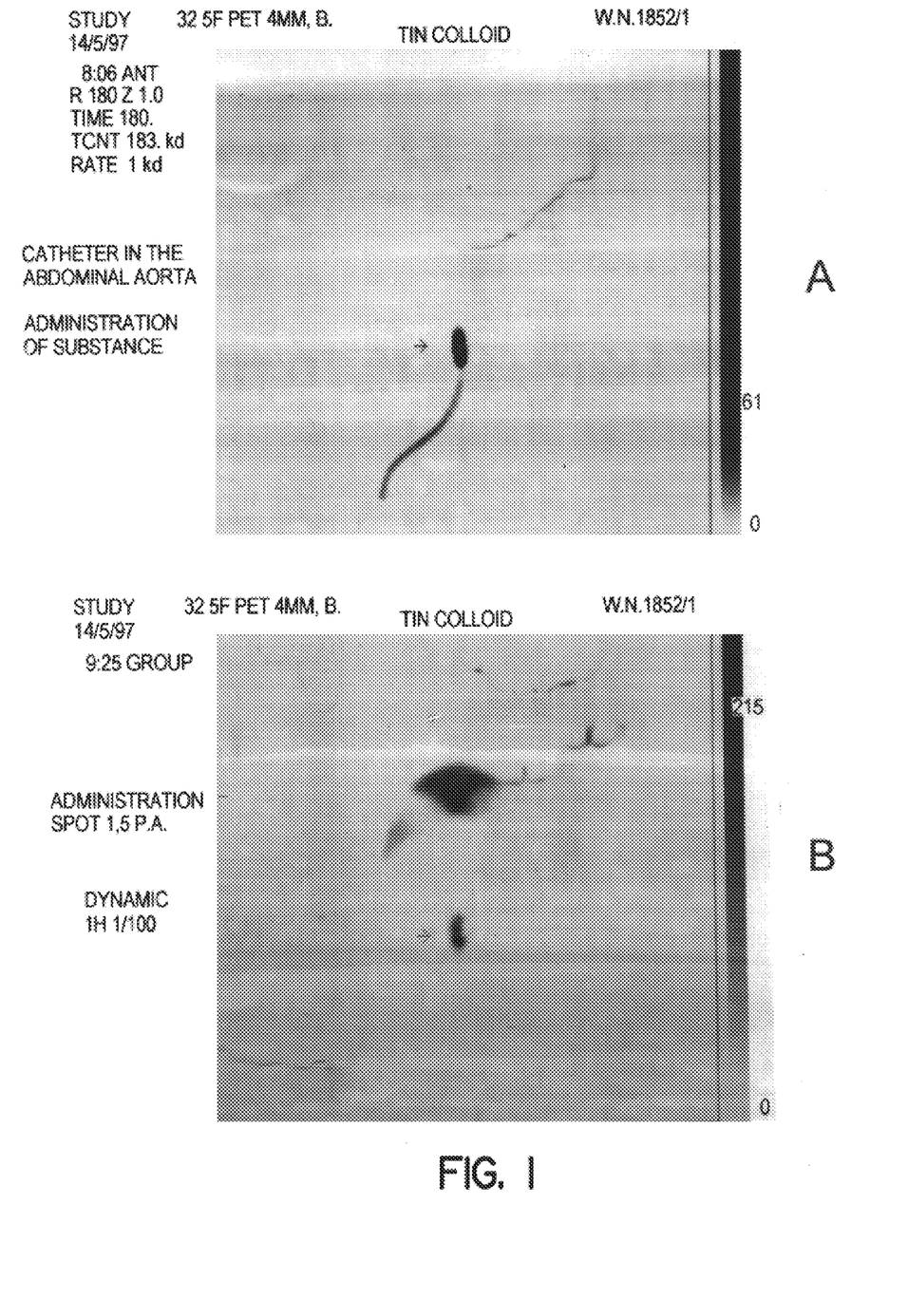
FIG. 1A shows an image of the body prior to administration of the radioactive substance. The arrow shows the balloon of the catheter.
FIG. 1B shows the same site 1.5 hours after administration and removal of the catheter. The amount of radioactive substance that remains at the adminstration site is clearly visible.

During the entire experiment, the test animal was under a gamma camera (Elscint SP4 HR) to display the dispersion of radioactivity in the body. In FIG. 1, the situation before administration is depicted in the upper part. The catheter that contains the tin colloid can be seen clearly. The arrow shows the balloon of the catheter, which is at the desired administration spot. In the lower part of the image, the same site is shown 1.5 hours after administration and removal of the catheter. The amount of tin colloid that remains at the administration spot is clearly visible.

EXAMPLE 15

Topical Administration of a Tin Colloid

The test animal is a white New Zealand rabbit (internal animal identification no.: 1839, male, 3.7 kg of body weight).

Under anesthesia (Rompun/Ketavet 1:2, 1 ml/kg of body weight, i.m. administration), the endothelium was damaged with a balloon catheter in the infraranal aorta (balloon denudation). Then, over a period of 5 minutes, tin colloid, which was produced according to the kit of the Amersham Company ("Amerscan Zinnkolloid ($^{99m}$Tc)— Markierungskit für die Leberszintigraphie") was administered to the test animal with a microperforated Match catheter (balloon catheter with a 5 mm diameter; manufacturer: Schneider Company, Düsseldorf). The radioactive dose of 0.47 mCi (=17.39 MBq) was administered in a volume of 0.1 ml.

Figure 2:
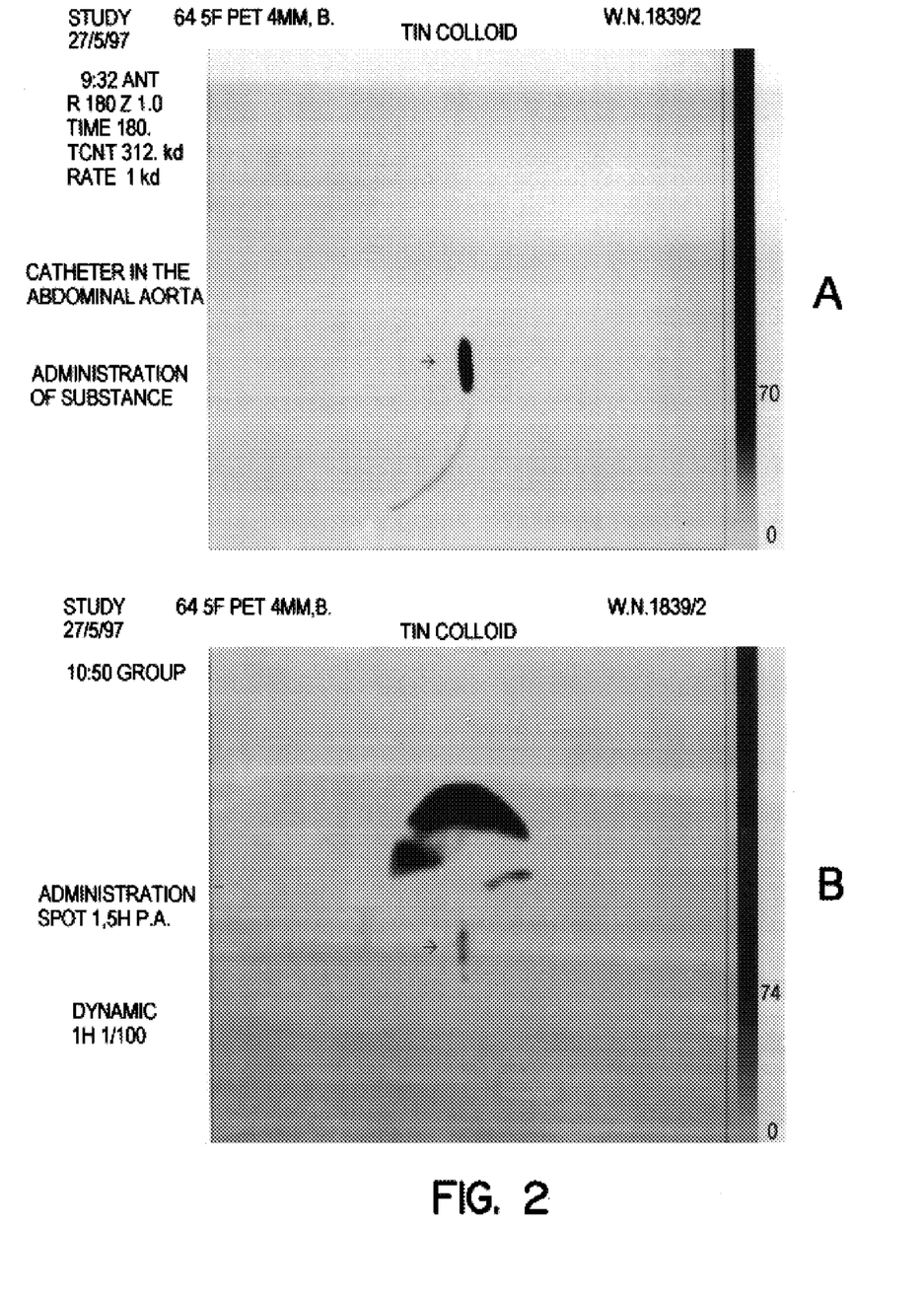
FIG. 2A shows an image of the body prior to administration of the radioactive substance. The arrow shows the balloon of the catheter.
FIG. 2B shows the same site 1.5 hours after administration and removal of the catheter. The amount of radioactive substance that remains at the administration site is clearly visible.

During the entire experiment, the test animal was under a gamma camera (Elscint SP4 HR) to display the dispersion of radioactivity in the body. In FIG. 2, the situation before administration is depicted in the upper part. The catheter that contains the tin colloid can be seen clearly. The arrow shows the balloon of the catheter, which is at the desired administration spot. In the lower part of the image, the same site is shown 1.5 hours after administration and removal of the catheter. The amount of tin colloid that remains at the administration spot is clearly visible.

What is claimed is:

1. A process for therapeutic treatment of proliferative diseases, comprising:

placing an administration catheter on the site of the lesion associated with said proliferative disease and administering topically via the catheter a radioactive substance by placing said substance in direct contact with said lesion, removing said catheter, wherein when the catheter is removed, the radioavtive substance remains on the site of the lesion and passes into a wall of said lesion.

2. A process for therapeutic treatment of arteriosclerotic diseases, comprising:

first an administration catheter in an ateriosclerotically altered vessel on the site of a lesion associated with said arteriosclerotic disease and administering topically via the catheter a radioactive substance by placing said substance in direct contact with said lesion, removing said catheter, wherein when the catheter is removed, the radioactive substance remains on the site of the lesion and passes into a wall of the alteriosclerotically altered vessel.

3. A process according to claim 2, wherein the radioactive substance is a metal complex.

4. A process according to claim 2, wherein the radioactive substance is a metal complex, whose ligand is a bis-amine-oxime derivative of general formula I, (I)

in which n=0–3, and radicals $R^1$ to $R^8$ are the same or different and in each case are a hydrogen atom and/or an unbranched, branched, cyclic or polycyclic $C_1$–$C_{100}$ alkyl, $C_1$–$C_{100}$ alkenyl, $C_1$–$C_{100}$ alkinyl, $C_1$–$C_{100}$ aryl, $C_1$–$C_{100}$ alkylaryl and/or $C_1$–$C_{100}$ arylalkyl radical, which optionally is substituted with fluorine, chlorine, bromine and/or iodine atoms, and/or hydroxy, oxo, carboxy, aminocarbonyl, alkoxycarbonyl, amino, aldehyde or alkoxy groups with up to 30 carbon atoms and/or optionally is interrupted and/or substituted by one or more heteroatoms from the series N, P, As, O, S, Se, and wherein radicals $R^2$ and $R^3$, $R^4$ and $R^5$ as well as $R^6$ and $R^7$ together optionally are an oxygen atom, and whose central atom is a radionuclide of the elements of atomic numbers 27, 29–32, 37–39, 42–51, 62, 64, 70, 75, 77, 82 or 83.

5. A process according to claim 2, wherein the radioactive substance is a metal complex, whose ligand is an $N_2S_2$ derivative of formula II, (II)

wherein $R^9$ to $R^{20}$ are the same or different and are independently selected from the group consisting of a hydrogen, an unbranched, branched, cyclic or polycyclic $C_1$–$C_{100}$ alkyl, $C_1$–$C_{100}$ alkenyl, $C_1$–$C_{100}$ alknye, $C_1$–$C_{100}$ aryl, $C_1$–$C_{100}$ alkylaryl and $C_1C_{100}$ arylalkyl radical, which optionally is substituted with fluorine, chlorine, bromine and iodine, hydroxy, oxo, carboxy, aminocarbonyl, alkoxycarbonyl, amino, aldehyde or alkoxy groups with up to 30 carton atoms, or optionally is interrupted or substituted by one or more heteroatoms selected from the group consisting of N, P, As, O, S, and Se, and wherein radicals $R^{11}$ and $R^{12}$, $R^{13}$ and $R^{14}$, $R^{15}$ and $R^{16}$, as well as $R^{17}$ and $R^{18}$ together are an oxygen atom, and n, m and p, independently of one another, are 1 or 2, and whose central atom is a metal radionuclide of the elements of atomic numbers 27, 29–32, 37–39, 42–51, 62, 64, 70, 75, 77, 82 or 83.

6. A process according to claim 2 wherein the radioactive substance is a metal complex, whose ligand is an $N_2S_2$ derivative of formula III, (III)

wherein $R^{21}$ to $R^{32}$ are the same or different and independently are selected from the group consisting of a hydrogen, an unbranched, branched, cyclic or polycyclic $C_1$–$C_{100}$ alkyl, $C_1$–$C_{100}$ alkenyl, $C_1$–$C_{100}$ alknye, $C_1$–$C_{100}$ aryl, $C_1$–$C_{100}$ alkylaryl and $C_1$–$C_{100}$ arylalkyl radical, which optionally is substituted with fluorine, chlorine, bromine, iodine, hydroxy, oxo, carboxy, aminocarbonyl, alkoxycarbonyl, amino, aldehyde or alkoxy groups with up to 30 carton atoms, or optionally is interrupted or substituted by one or more heteroatoms selected from the group consisiting of N, P, As, O, S, and Se, and whose central atom is a metal radionuclide of the elements of atomic numbers 27, 29–32, 37–39, 42–51, 62, 64, 70, 75, 77, 82 or 83.

7. A process according to claim 4 wherein a central atom, which is selected from the group consisting of $^{99m}Tc$, $^{186}Re$, $^{188}Re$, $^{67}Cu$, $^{90}Y$ and $^{107}Ag$, and contains the metal complex that is used.

8. A process according to claim 2, wherein the radioactive substance is a metal complex, whose ligand is a porphyrin derivative.

9. A process according to claim 2, wherein the radioactive substance is a thallium compound of isotopes $^{201}$Tl $^{207}$Tl, $^{209}$Tl or $^{210}$Tl.

10. A process according to claim 2, wherein the radioactive substance is $^{201}$TlCl.

11. A process according to claim 2, wherein the radioactive substance is a tetrofosmin derivative.

12. A process according to claim 2, wherein the radioactive substance is a sestamibi derivative.

13. A process according to claim 2, wherein the radioactive substance is a furifosmin derivative.

14. A process according to claim 2, wherein the radioactive substance is a colloidal solution with particle sizes of 5–1000 nm.

15. A process according to claim 2, wherein the radioactive substance is $^{99m}$Tc-tin colloid or $^{186}$Re-tin colloid.

16. A process according to claim 2, wherein the catheter is a microporous balloon catheter.

17. A process according to claim 2, wherein the catheter is a multichamber balloon catheter.

* * * * *

UNITED STATES PATENT AND TRADEMARK OFFICE
CERTIFICATE OF CORRECTION

PATENT NO. : 6,436,365 B2  
DATED : August 20, 2002  
INVENTOR(S) : Ludger Dinkelborg et al.

It is certified that error appears in the above-identified patent and that said Letters Patent is hereby corrected as shown below:

Title page,  
Please insert the following after Item [22]:  
-- [30]  Foreign Priority Data - German Application No. DE 19742880, filed on September 23, 1997. --

Column 13,  
Line 22, reads "the radioavtive substance" should read -- the radioactive substance --  
Line 28, reads "first an administration" should read -- placing an administration --  
Line 35, reads "the alterioscleroticaly" should read -- the arteriosclerotically --

Column 14,  
Line 18, reads "alknye," should read -- alkyne, --  
Line 19, reads "C1C100 arylalkyl" should read -- C1-C100 arylalkyl --  
Line 20, reads "bromine and" should read -- bromine, --  
Line 23, reads "30 carton atoms," should read -- 30 carbon atoms, --  
Line 51, reads "alknye," should read -- alkyne, --  
Line 55, reads "30 carton atoms," should read -- 30 carbon atoms, --  
Lines 56-57, reads "consisiting" should read -- consisting --  
Line 61, reads "claim 4" should read -- claim 4, --

Column 15,  
Line 2, reads "201T1 207T1," should read -- 201T1, 207T1, --

Signed and Sealed this

First Day of June, 2004

JON W. DUDAS  
*Acting Director of the United States Patent and Trademark Office*